United States Patent [19]

Tabibi et al.

[11] Patent Number: 5,130,122
[45] Date of Patent: Jul. 14, 1992

[54] ORAL CAVITY AND DENTAL MICROEMULSION PRODUCTS

[75] Inventors: Esmail Tabibi, Chelmsford; Arthur A. Siciliano, Framingham, both of Mass.

[73] Assignee: MediControl Corporation, Newton, Mass.

[21] Appl. No.: 581,025

[22] Filed: Sep. 12, 1990

Related U.S. Application Data

[62] Division of Ser. No. 303,479, Jan. 27, 1989, Pat. No. 4,971,788.

[51] Int. Cl.$^5$ .......................... A61K 7/16; A61K 9/10
[52] U.S. Cl. ........................ 424/49; 514/938; 514/943; 514/900; 514/901; 514/902; 424/56; 424/58
[58] Field of Search .................. 424/49, 58, 195.1, 56; 514/900, 901, 902, 938, 943; 44/301

[56] References Cited

U.S. PATENT DOCUMENTS

| | | | |
|---|---|---|---|
| 884,878 | 4/1908 | van der Ploeg | 44/301 |
| 1,347,734 | 7/1920 | De Cew | 44/301 |
| 1,498,340 | 6/1924 | Belknap | 44/301 |
| 1,533,158 | 4/1925 | Belknap | 44/301 |
| 1,614,735 | 1/1927 | Kirschbraun | 44/301 |
| 3,201,353 | 8/1965 | Corben | 44/301 |
| 3,540,866 | 11/1970 | Miller | 44/301 |
| 3,902,869 | 9/1975 | Friberg et al. | 44/301 |
| 4,115,313 | 9/1978 | Lyon et al. | 44/301 |
| 4,244,702 | 1/1981 | Alliger | 44/301 |
| 4,590,065 | 5/1986 | Piechota et al. | 424/58 |
| 4,606,913 | 8/1986 | Aronson et al. | 424/59 |
| 4,687,663 | 8/1987 | Schaeffer | 514/902 |
| 4,874,547 | 10/1989 | Narula | 514/941 |
| 4,971,788 | 11/1990 | Tabibi et al. | 424/49 |
| 4,980,154 | 12/1990 | Gordon | 514/902 |

FOREIGN PATENT DOCUMENTS 29332  5/1981  European Pat. Off. .

Primary Examiner—Ronald W. Griffin
Attorney, Agent, or Firm—Bruce F. Jacobs

[57] ABSTRACT

Oral cavity and dental products are prepared by microemulsifying an adsorptive oil in an aqueous medium to produce uniform submicron sized droplets. The products avoid the generally unaesthetic, oily, and unpleasant taste problems of previous similar products.

15 Claims, No Drawings

ORAL CAVITY AND DENTAL MICROEMULSION PRODUCTS

This is a divisional of copending application(s) Ser. No. 07/303,479 filed on Jan. 27, 1989, now U.S. Pat. No. 4,971,788.

BACKGROUND OF THE INVENTION

This invention relates generally to the preparation and composition of oral cavity and dental products. More specifically, it relates to products intended to remove bacteria and other microbes from teeth surfaces and the oral cavity to thereby reduce malodor and ameliorate other microbial induced disease states.

Oral cavity malodor ("halitosis" or "bad breath") is caused not only by the odors of food previously eaten but also by the actions of various microorganisms on the ingested material which produce odorous sulfur-containing chemicals. The traditional products currently available for treating oral cavity malodor typically contain fragrant aromatic flavor oils to mask the malodor. In addition, they often contain one or more alcohols, abrasives, antimicrobial agents, and detergents which are believed to inhibit action of the microorganisms on ingested material by enhancing the removal of such material from tooth surfaces or by exerting a microbicidal or static effect. These products conventionally have the form of mouthwashes, sprays, gels, pastes and the like.

Furthermore, similar compositions have been utilized to inhibit other oral cavity microorganisms which can cause conditions such as dental cavities, plaque formation, gingivitis, and the like. Heretofore, these compositions have been generally aqueous/alcoholic solutions containing small amounts of aromatic flavor oils dissolved therein along with one or more alcohols, abrasives, antimicrobial agents, and detergents. These products have also been formed as semisolid products by incorporating conventional water-soluble gelling agents.

Tooth pastes have traditionally been solid dispersions of abrasives, flavors, detergents, antimicrobial agents, fluorides, sweeteners and the like.

These products have specific limitations which restrict their use. For instance, the alcohols can be irritating to portions of the oral cavity, particularly to abraded areas. Other products containing high levels of detergents can cause adverse effects such as gum recession, edema, local irritations, and even allergic reactions. Moreover, the malodor and microbial suppression is generally found to remain for a quite short period of time.

One attempt at overcoming some of these problems is disclosed in U.S. Pat. No. 4,525,342 which teaches the effectiveness of certain hydrocarbon and fixed vegetable oils in desorbing and binding oral cavity microbes which cause malodor and disease. The compositions comprise two phases, one an oily phase and the other an aqueous phase, which are mixed just prior to use, generally by swishing in the mouth. Such a product suffers from the disadvantage of being unaesthetic, oily, and unpleasant to the taste. In addition, it requires a special dispenser to accurately meter the correct proportion of each phase into the mouth on a consistent basis. The crude emulsion formed by swishing in the mouth of the user in the absence of emulsifiers will inherently consist of very large oil droplets, typically in the 10 to 100 micron range. Also since people vary significantly in their swishing action, there will be a significant variation in effectiveness of the product.

Accordingly, it is an object of the present invention to produce fluid, gel, or paste emulsions having essentially uniform submicron size to be used in the oral cavity to reduce malodor and to ameliorate microbe-mediated diseases.

It is a further object to produce such products having enhanced effectiveness, reduced irritation potential, sustained duration of action, extended shelf life, pleasant taste and appearance characteristics.

These and other advantages will be apparent from the detailed description of the invention below.

SUMMARY OF THE INVENTION

It has been discovered that oral cavity and dental products comprised of uniform submicron adsorptive oil particles uniformly distributed in an aqueous phase produce improved removal of odorous compounds, odor-causing bacteria, and disease-causing microbes. The products of this invention are prepared by subjecting a mixture of at least an adsorptive oil, water, and an emulsifier to ultra high energy mixing, i.e. Microfluidizer ® processing. Optionally, other water-soluble, oil-soluble, or amphiphilic materials may also be present.

DESCRIPTION OF THE PREFERRED EMBODIMENTS

The oral cavity and dental products of the present invention are uniform submicron adsorptive oil particles uniformly dispersed in an aqueous phase.

The adsorptive oils suitable for use herein include physiologically acceptable hydrocarbons, vegetable oils, mineral oils, fish oils, animal oils, semi-synthetic and synthetic analogs thereof, and mixtures thereof. The adsorptive oils have been shown to be effective for the removal of the unpleasant odor from saliva samples which have been allowed to putrify. Preferably the adsorptive oil is selected from corn oil, olive oil, coconut oil, soya bean oil, safflower oil, decane, dodecane, tetradecane, hexadecane, white mineral oil, and mixtures thereof.

Emulsifiers suitable for use herein to form the emulsified oils include the conventional physiologically acceptable emulsifiers generally recognized as safe for human consumption. Examples of suitable emulsifiers include those of the general classes of anionic, cationic, and nonionic emulsifiers appropriate for use in the oral cavity or generally recognized as safe in 21 CFR 170-1999 and other parts of the CFR. Specific examples of suitable emulsifiers include lecithin, saponins, sodium lauryl sulfate, sodium lauryl sarcosinate, cetyl pyridinium chloride, glyceryl esters, sorbitan esters, polyoxyethylene sugar esters, block copolymers of propylene-/ethylene oxide, and the like. The emulsifiers may be used singly or in mixtures. Generally the total emulsifier content will be on the order of about 0.01 to about 10.0 percent by weight based on the weight of the product. Preferable amounts of emulsifier will be about 0.05 to about 5.0 weight percent. Most preferably the amounts will be about 0.1 to about 2.0 weight percent.

In addition to the adsorptive oil and emulsifier, the present oral cavity and dental products may contain one or more water-soluble, oil-soluble, or amphiphilic materials which are conventionally incorporated in such products. For instance, the products may contain antimicrobials, antifungals, fluorides, preservatives, sweeteners, flavors, chelating agents, colors, stabilizers, thickeners, abrasives, bulking agents, emollients, aromatics, desensitizers, antioxidants, and the like. These materials, when present, are used in their conventional amounts, i.e. up to about 50 weight percent of the total composition, though generally in much lower amounts.

To commence the preparation of the uniform submicron adsorptive oil particles uniformly dispersed in an aqueous phase, the basic oil phase is first prepared. Thus, any oil-soluble components in the desired product are mixed together with the adsorptive oil to form an oil phase. The aqueous phase optionally containing any water-soluble components (generally other than the thickeners and/or bulking agents) is prepared by dissolving in at least a minor portion of the total water to be used to form an aqueous phase. Alternatively, the other water-soluble components may be added to the uniform submicron emulsion produced herein. Any amphiphilic materials to be included may be added to either the oil or aqueous phase though generally they will be included in the aqueous phase as this has been found to make formation of the emulsified adsorptive oil particles more efficient. Thereafter, the aqueous phase is generally added to the oil phase (though reverse addition could also be used) with conventional mixing, e.g. a propellar mixer, to form a crude emulsion similar to what would be formed in a person's mouth by swishing. Any water not included in the preliminary aqueous phase above is then added to dilute the composition to the desired concentration.

To convert the crude initial emulsion above to the uniform submicron emulsion of the present invention the crude emulsion is subjected to an ultra high energy mixing device, i.e. a Microfluidizer which can generally form microemulsions showing limited stability in the absence of an emulsifier. A particularly suitable such device is available from Microfluidics Corporation, Newton, MA, and is described in U.S. Pat. No. 4,533,254, the subject matter of which is hereby incorporated by reference. The ultra high energy mixing device serves to convert the crude oil-in-water emulsion to a uniform emulsion containing submicron sized oil-phase particles without requiring further size alteration or separation. Typical process conditions for the Microfluidizer ® process equipment include operating pressures of about 2,000 to about 20,000 psi and at least one cycle/pass through the equipment. External process temperatures may be varied from just above the freezing point of the crude emulsion to just below its boiling point, preferably in the range of about 4° C. to about 50° C.

Upon passing the crude emulsion through the device, the result is a uniform oil-in-water emulsion wherein the oil phase particles have a submicron particle size (as determined by conventional quasi elastic laser light scattering particle size determination instruments) and a narrow size distribution. While a single pass through the Microfluidizer ® process equipment will form a relatively uniform composition, it has been found to be more advantageous to use multiple passes to further decrease the size of the oil phase particles and to increase the uniformity of the resultant oral cavity and dental emulsion products. Accordingly, it is preferable to subject the crude emulsion to about 2 to about 5 passes, though 2 to about 4 passes will produce sufficient uniformity for most applications.

The Microfluidizer process equipment allows easy preparation of a uniform submicron oil-in-water emulsion which enhances the effectiveness of the oral cavity and dental product as compared to non-uniform relatively large emulsions. In addition, the equipment is capable of handling varying flow rates ranging from about several hundred milliliters per minute in a laboratory scale device to over 50 gallons per minute in a full production scale device.

The oil-in-water emulsions produced herein contain submicron sized oil particles uniformly distributed in the aqueous phase. Preferably the oil particles have mean effective diameters less than about 0.5 microns and a size distribution less than ±60%. Most preferably, the emulsified oil particles will have mean effective diameters less than about 0.3 microns and a size distribution less than ±50%.

If it is desired to thicken the emulsion to form a more viscous product, even a gel or a paste, the desired thickener or bulking agent (along with any water-soluble components not included in the initial aqueous phase used to prepare the submicron emulsions) may be slowly added to the submicron emulsion with stirring.

It has been discovered that by using a uniform submicron emulsified adsorptive oil in place of the crude, non-uniform, large oil particles, improved products having increased sorption and binding activity result. Hence, the products of the present invention exhibit longer levels of higher activity than the previous ones.

The improved oral cavity and dental products which are prepared herein include mouthwashes, non-abrasive dentifrice gels, abrasive toothpastes and the like. As these products have been prepared before, but not containing the uniform submicron emulsions of the present invention, further details on them is readily available in the prior art and is not repeated here. Any conventional additives useful in these products may also be incorporated in the present products by dissolving it in either the oil or aqueous phases prior to the emulsion formation.

The practice of this invention is illustrated by, but not limited to, the following examples in which all parts and percents are by weight unless otherwise specified.

EXAMPLE I

Preparation and Evaluation of Mouthwash

To prepare a mouthwash in accordance with this invention, an oil phase is prepared containing the following ingredients in the stated percents of the final mouthwash:

| Ingredient | Percent |
| --- | --- |
| Corn oil | 10.0 |
| Glyceryl monooleate | 0.3 |
| Octaglyceryl monooleate | 0.7 |
| t-Butylhydroquinone | 0.001 |
| Spearmint flavor | 1.0 |
| Methyl paraben | 0.1 |

An aqueous phase is prepared containing:

| Ingredient | Percent |
| --- | --- |
| Water, deionized | 10.0 |
| Sodium saccharine | 0.02 |
| Cetyl pyridinium chloride | 0.05 |

The oil phase is added to the aqueous phase with propellar mixing. Then additional deionized water (77.25%) is added with continued mixing to form a crude emulsion containing oil particles ranging in size from submicron to greater than 75 microns, predominantly in the range of 10 to 100 microns. This crude emulsion is pressure fed to a laboratory scale Microfluidizer® M-110 device (Microfluidics Corp., Newton, MA) set to operate at 12,000 psi at room temperature (23° C.). After three passes through this equipment a homogeneous submicron oil-in-water emulsion resulted. Three passes are used to increase the uniformity and to reduce the size of the oil particles therein.

To thicken the emulsion methyl cellulose (0.4%) is slowly added using a propellar mixer.

Analysis of the resulting microemulsion using a quasielastic laser light scattering particle size determination instrument (Brookhaven Instruments, Model BI-90, Brookhaven, NY) shows an average oil droplet size of 0.17 microns with a size distribution of ±39%.

To evaluate the effectiveness of the above prepared mouthwash as compared to a crude emulsion thickened to the same extent, polystyrene test surfaces are prepared and bacteria are bound thereto. The degree of effectiveness is determined by contacting the test surfaces with the two emulsions. The emulsion of the present removes a substantially greater percentage of the bound bacteria than does the crude emulsion.

EXAMPLE II

Preparation of Mouthwash

The procedure of Example I is repeated to produce another mouthwash containing the following ingredients in the oil phase:

| Ingredient | Percent |
| --- | --- |
| Safflower oil | 5.0 |
| Mineral oil | 5.0 |
| Sodium lauryl sulfate | 0.16 |
| t-Butylhydroquinone | 0.001 |
| Methyl paraben | 0.10 |
| Peppermint flavor | 1.0 | and the following ingredients in the aqueous phase:

| Ingredient | Percent |
| --- | --- |
| Sodium saccharine | 0.02 |
| Glycerine | 5.0 |
| Water, deionized | 10.0 |

After combining the two phases as in Example I, the balance of the deionized water (73.67%) is added and the resulting crude emulsion processed through the Microfluidizer three times at an operating pressure of 10,000 psi. The resultant mouthwash contains oil droplets/particles having an average mean diameter of 0.20 microns with a size distribution of ±36%. Comparative testing of the effectiveness of this emulsion as compared to the crude emulsion shows a similar level of improvement in removing bacteria as in Example I.

EXAMPLE III

Preparation of Non-Abrasive Dentifrice Gel

The basic procedure of Example I is repeated to produce a non-abrasive dentifrice gel. The oil phase consists of:

| Ingredient | Percent |
| --- | --- |
| Corn oil | 20.0 |
| Sodium lauryl sulfate | 1.0 |
| t-Butylhydroxyquinone | 0.0001 |
| Methyl paraben | 0.10 |
| Peppermint flavor | 1.0 | and the aqueous phase consists of:

| Ingredient | Percent |
| --- | --- |
| Sorbitol solution (85%) | 5.0 |
| Sodium saccharine | 0.05 |
| Water | 21.85 |

After combining the two phases as in Example I, the resulting crude emulsion is processed through the Microfluidizer three times at an operating pressure of 14,000 psi. The resultant non-abrasive dentifrice gel contains oil droplets/particles having an average mean diameter of 0.27 microns with a size distribution of ±43%. Thereafter, the balance of the deionized water (50.0%) containing dissolved therein a cellulose gum (1.5%) is added using an anchor mixer.

EXAMPLE IV

Preparation of Abrasive Toothpaste

To prepare an abrasive toothpaste, 20 g of ultrafine dicalcium phosphate is added to 80 g of the dentifrice gel of Example III using an anchor mixer. The resulting suspensoid emulsion paste is then passed through a colloid mill to make it more uniform.

COMPARATIVE EXAMPLE A

The procedure of Example I is repeated in the absence of any emulsifier, i.e. the two monooleates are omitted. When the oil phase and the aqueous phase are mixed the result is immediate separation upon cessation of mixing. When this material is processed through the Microfluidizer equipment, the result is an emulsion which separates after standing for several hours. This shows that the presence of an emulsifier is necessary for the preparation of the products of this invention even though the Microfluidizer is capable of preparing a microemulsion showing limited stability in the absence of any emulsifiers. In addition, it shows that the presence of the emulsifier during submicron emulsion formation is not detrimental to the operation of the Microfluidizer.

What is claimed is:

1. An improved dental and oral hygiene product adapted to remove odorous compounds, odor-causing bacteria, and other oral disease causing microbes from an oral cavity and teeth when placed in contact with the product, wherein the product comprises a stable uniform submicron emulsion of an adsorptive oil in an aqueous medium and further contains one or more sweeteners, flavors, chelating agents, colors, stabilizers, thickeners, antioxidants, abrasives, bulking agents, emollients, aromatics, desensitizers, surfactants, and therapeutic agents; and wherein the product is not a high internal phase emulsion.

2. The product of claim 1 wherein the adsorptive oil is selected from the group consisting of vegetable oils, mineral oils, fish oils, animal oils, semi-synthetic and synthetic analogs of said oils, and mixtures thereof.

3. The product of claim 1 wherein the adsorptive oil is selected from the group consisting of corn oil, olive oil, coconut oil, soya bean oil, safflower oil, decane, dodecane, tetradecane, hexadecane, white mineral oil, and mixtures thereof.

4. The product of claim 1, wherein the adsorptive oil is in the form of particles having an average mean diameter of less than about 0.5 microns with a size distribution of about ±60%.

5. The product of claim 1, wherein the adsorptive oil is in the form of particles having an average mean diameter less than about 0.3 microns with a size distribution of about ±50%.

6. The product of claim 1, wherein the therapeutic agent is an antimicrobial agent.

7. The product of claim 1, wherein the therapeutic agent is an antifungal agent.

8. The product of claim 1, wherein the therapeutic agent is an anti-cavity agent.

9. The product of claim 1 in the form of a mouthwash.

10. The product of claim 1 in the form of a non-abrasive dentifrice gel.

11. The product of claim 1 in the form of an abrasive toothpaste.

12. The product of claim 1, further containing an emulsifier.

13. The product of claim 12 wherein the emulsifier is selected from the group consisting of lecithin, saponins, sodium lauryl sulfate, sodium lauryl sarcosinate, cetyl pyridinium chloride, glyceryl esters, sorbitan esters, polyoxyethylene sugar esters, block copolymers of propylene/ethylene oxide, and mixtures thereof.

14. The product of claim 12 wherein the emulsifier is present in an amount of about 0.05 to about 5 wt % based on the weight of the product.

15. The product of claim 12 wherein the emulsifier is present in an amount of about 0.1 to about 2 wt % based on the weight of the product.

* * * * *